US010912698B1

(12) United States Patent
Termanini

(10) Patent No.: US 10,912,698 B1
(45) Date of Patent: Feb. 9, 2021

(54) TABLE ATTACHMENT FOR DIRECT ANTERIOR SURGICAL APPROACH OF THE HIP

(71) Applicant: Zafer Termanini, Port Saint Lucie, FL (US)

(72) Inventor: Zafer Termanini, Port Saint Lucie, FL (US)

( * ) Notice: Subject to any disclaimer, the term of this patent is extended or adjusted under 35 U.S.C. 154(b) by 0 days.

(21) Appl. No.: 16/732,044

(22) Filed: Dec. 31, 2019

(51) Int. Cl.
*A61G 13/12* (2006.01)
*A61G 13/08* (2006.01)

(52) U.S. Cl.
CPC ........... *A61G 13/123* (2013.01); *A61G 13/08* (2013.01); *A61G 13/125* (2013.01); *A61G 13/1295* (2013.01); *A61G 2210/10* (2013.01)

(58) Field of Classification Search
CPC ...... A61G 13/08; A61G 13/12; A61G 13/123; A61G 13/125; A61G 13/1295
See application file for complete search history.

(56) References Cited

U.S. PATENT DOCUMENTS

| 2005/0222573 A1* | 10/2005 | Branch | A61B 17/154 606/86 R |
| 2007/0089239 A1* | 4/2007 | Whiteside | A61G 13/12 5/624 |

* cited by examiner

*Primary Examiner* — Fredrick C Conley
(74) *Attorney, Agent, or Firm* — Samir Termanini, Esq.

(57) ABSTRACT

A surgical table attachment for providing hyperextension of the hip joint during direct anterior approach without need for lowering the distal end of the operating table. The attachment will allow external rotation as well as adduction for better exposure of the proximal end of the femur. It further allows for motorized traction of the lower extremity controlled by the operating surgeon. The inventive device conveniently incorporates a femoral elevator mechanism that will raise the proximal end of the femoral bone for better visualization through the wound and easier reduction of the implant. The device is easily used with any conventional surgical table and can made from radiolucent material allowing intraoperative X-ray control.

19 Claims, 12 Drawing Sheets

TABLE ATTACHMENT FOR DIRECT ANTERIOR SURGICAL APPROACH OF THE HIP

FIELD OF THE INVENTION

The present invention relates to a surgical table attachment and more particularly to an attachment used to facilitate the visualization of the hip anatomy during Direct Anterior surgical approach to the hip.

DESCRIPTION OF THE PRIOR ART

Total hip replacement surgery has been successfully used for several decades. Carl Hueter first described the anterior approach in 1881. It was later popularized in Europe by Robert Judet and in the United States by Smith Peterson. The direct anterior approach to the hip has been suggested to have several advantages compared to previously popular approaches due to the use of Intramuscular and intra nervous interval between the Tensor Fascia Latae and Sartorius Muscle. In view of the tissue sparing and minimally invasive benefits, direct anterior total hip arthroplasty has gained popularity in recent years and has given rise to a sharp increase in its utilization. The procedure requires using specialty designed table as well as special instruments. However, many authors have also performed the procedure using a regular table and commonly used arthroplasty tools. Proper surgical technique and limb positioning are vital to reduce the risk of intra operative complication, such as femoral fracture or damage to surrounding soft tissues. Specialty design tables, such as the Hannah table are extremely expensive and necessitate the help of extra personnel to manipulate the table and operated extremity. These tables and their attachments are cumbersome and require large space for storage. In addition, in order to provide extension of the hip joint for exposing the proximal end of the femur, the operated leg is often lowered down, where the foot becomes very close to the floor thereby increasing chance of contamination of the sterile drapes and operative field. Another critical challenge during the surgical procedure is to raise the proximal femoral end so the medullary canal can be reamed. Retractors and bone hooks are usually used to elevate the femur; however, any excessive traction may cause a femoral fracture, especially in the thin osteoporotic bone. More elaborate femoral bone mechanical elevators attachment has been designed, such as the Wixson Anterior suspension Hook System. These are usually attached to a table, but they are expensive, cumbersome, and may get in the way of the surgeon. Undue traction may also cause fracture of the femoral bone.

The present disclosure describes a surgical table attachment, which provides a safe extension of the hip as well as a mechanism to raise the proximal end of the femoral bone without the use of traction bone hooks or other suspension devices.

SUMMARY OF THE INVENTION

In view of the foregoing disadvantages inherent in the known type of surgical tables used for the anterior approach, and attached femoral bone traction and elevator devices now present in the prior art, the present invention provides a new surgical table attachments and femoral bone elevator that can be adapted for usage with any conventional surgical table to perform hip replacement through a small incision using minimally invasive anterior surgical approach.

The general purpose of the present invention, which will be described subsequently in greater detail, is to provide a novel attachment that has many advantages of the existing specialized surgical tables and many novel features that result in a new Device which is not anticipated, rendered obvious, suggested, or even implied by any of the prior on either alone or in any combination thereof.

To attain this, the present invention generally comprises a base platform, which would be attached to the operative table and an upper folding platform having two segments. Namely, a proximal segment (for the torso and a lumbar region) and a lower segment (for the lower extremities.) The junction between the two segments will be raised mechanically causing the upper platform to fold. A central post is vertically situated in the middle of the folding portion and firmly attached to the center of the lower portion of the platform. Said central post houses the electromechanical lifting mechanism. Said lifting mechanism is powered by electric motor.

The electromechanical lifting mechanism comprises a central pole and a coaxial gliding cylinder. The gliding cylinder comprises two diametrically opposed horizontal lifting rods situated at the fold between the lumbar and the lower extremity segments. When the electric motor is powered, it turns a central rotating shaft, this in fact will move a centrally threaded carriage to which the coaxial gliding cylinder is it attached via sliding pins. Said coaxial gliding cylinder has two diametrically opposed horizontal lifting rods threaded into a lifting ring situated at the lower end of the gliding cylinder. It is to be understood that when the electric motor turns the central rotating threaded shaft, this will raise the centrally threaded gliding plate lifting rod and fold the upper platform.

Furthermore, the lower extremity segment comprises an attachment to secure the foot of the operated side. Said attachment will provide a mechanism for traction as well as internal or external rotation of the foot attachment. These movements are important steps during the anterior surgical approach. The traction applied to the lower extremity is provided by a worm gear attached to an electric motor situated within an extension tube between the foot attachment and the lower extremity platform. The traction motor can have its own rechargeable power supply conveniently located inside the extension tube. The operating surgeon can control it by using a traction in/out switch located on the extension tube and it can be easily accessed by the surgeon without the need for additional personnel to manipulate the foot attachment. The lower foot attachment also allows for adduction or abduction providing improved exposure of the proximal femur through the small surgical incision.

After the removal of the femoral head, the proximal end of the femoral bone is now located deep in the surgical wound and reaming of the femur is quite difficult due to poor exposure of the canal. It is therefore significantly advantageous to raise the proximal end of femur and elevate it through the wound. Once the neck of the femur is cut and osteotomized, its proximal end becomes mobile since the anterior capsule is released and detached. Upward pressure on the posterior surface of the thigh will force the proximal end of the femur to rise upward, and its end, to protrude through the surgical wound, which will facilitate the intramedullary reaming process of the femoral bone. It is therefore unnecessary to use hooks and lifting devices to lift the proximal end of the femur since these devices may lead to undue stress on the femoral bone causing complications such as fractures.

There has thus been outlined, rather broadly, the more important features of the invention in order that the detailed description thereof may be better understood. Additional features of the invention are described hereinafter. For example, the motorized portion of the central post can be replaced with mechanical mean such as manual crank (not illustrated).

In this respect, before explaining that preferred embodiment of the present invention in detail, it is to be understood that the invention is not limited in its application through the details of construction and arrangement of its components set forth in the following description or illustration. It is also to be understood that phraseology employed herein for the purpose of the description should not be regarded as limiting.

The present disclosure provides a surgical table attachment that overcomes prior shortcomings of prior art devices because it facilitates the surgical approach to the proximal end of the femoral bone after the removal of the femoral head. The attachment described in this invention can be easily adapted for usage with any conventional operating table commonly used in operating rooms.

Other objects and advantages of the present invention will become obvious to the reader and it is intended that these objects and advantages are within the scope of the present invention.

To the accomplishment of the above and related objects, this invention may be embodied in the form elicited in the accompanying drawings, attention being called to the fact, however, that the drawings are illustrative only and that changes may be made in the specific construction illustrated.

BRIEF DESCRIPTION OF THE DRAWINGS

The present invention can be easily understood by creating that subsequent detailed description of the preferred embodiment thereof with references made to the accompanying drawings, wherein.

DETAILED DESCRIPTION OF THE INVENTION

Turning now descriptively to the drawings, in which similar references characters denote similar elements throughout the several views, the attached figures illustrate the operative table attachment device and its components.

Figure 1:
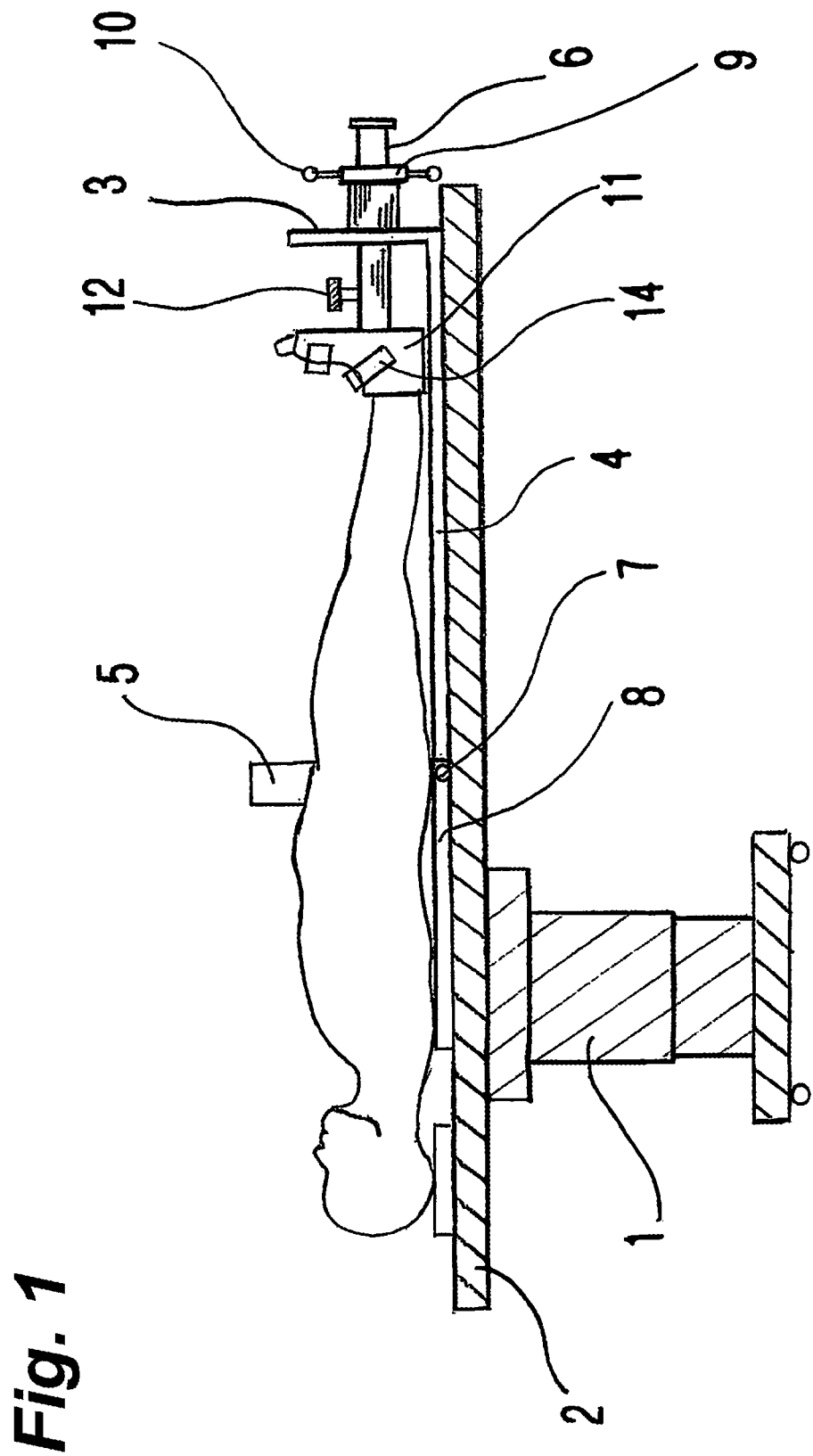
FIG. 1 is a side view of operating table and attachment in flat position.

Referring to FIG. 1, The patient is placed in supine position over the device, which is placed over the flat surface of operative table 2. Hydraulic unit 1 raises or lowers the operating table. The foot on the operative side is placed in boot 11, secured with Velcro straps 14. Vertical central post 5 is positioned between the legs and secured to the device. Foot boot 11 is attached to traction mechanism having threaded rod 6 and tightening nut 10. Said boot 11 is capable of axial rotation to the right or left and can be locked in position using locking knob 12.

Figure 2:
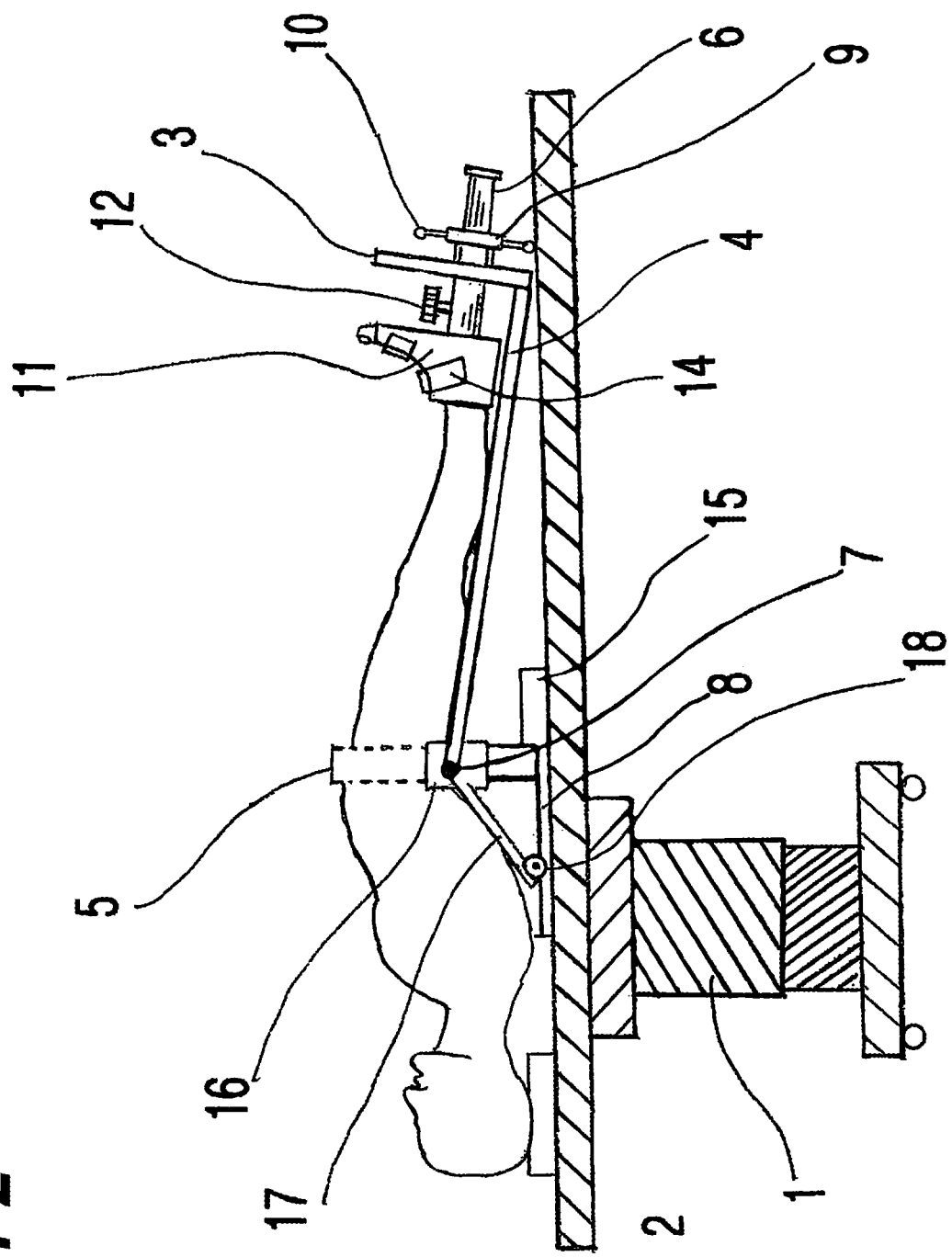
FIG. 2 is a side view of operating table and attachment in flexed position.

Now referring to FIG. 2, where the lifting mechanism in central post 5 is activated via motor 15 which raised the pelvic bone of the patient causing proximal torso plate 17 and distal lower extremity plate 4 to rise. This will cause the device to flex at the level of hinge 7. The proximal torso plate 17 is attached distally to lifting rods 51 (see FIG. 7) and proximally has rollers 18 for facilitating gliding over baseplate 8.

Figure 3:
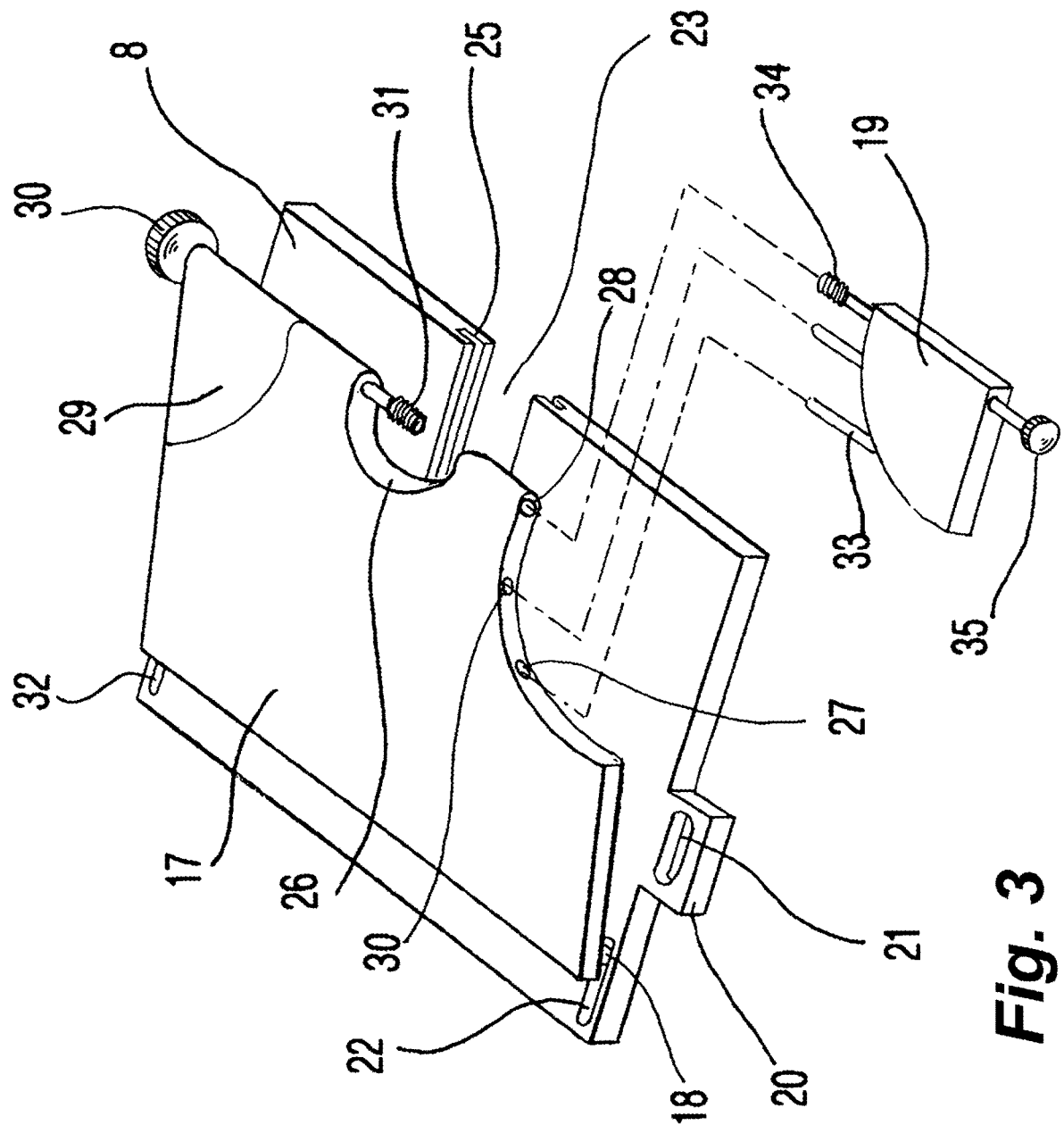
FIG. 3 is a perspective view of the proximal torso trays.
Figure 4:
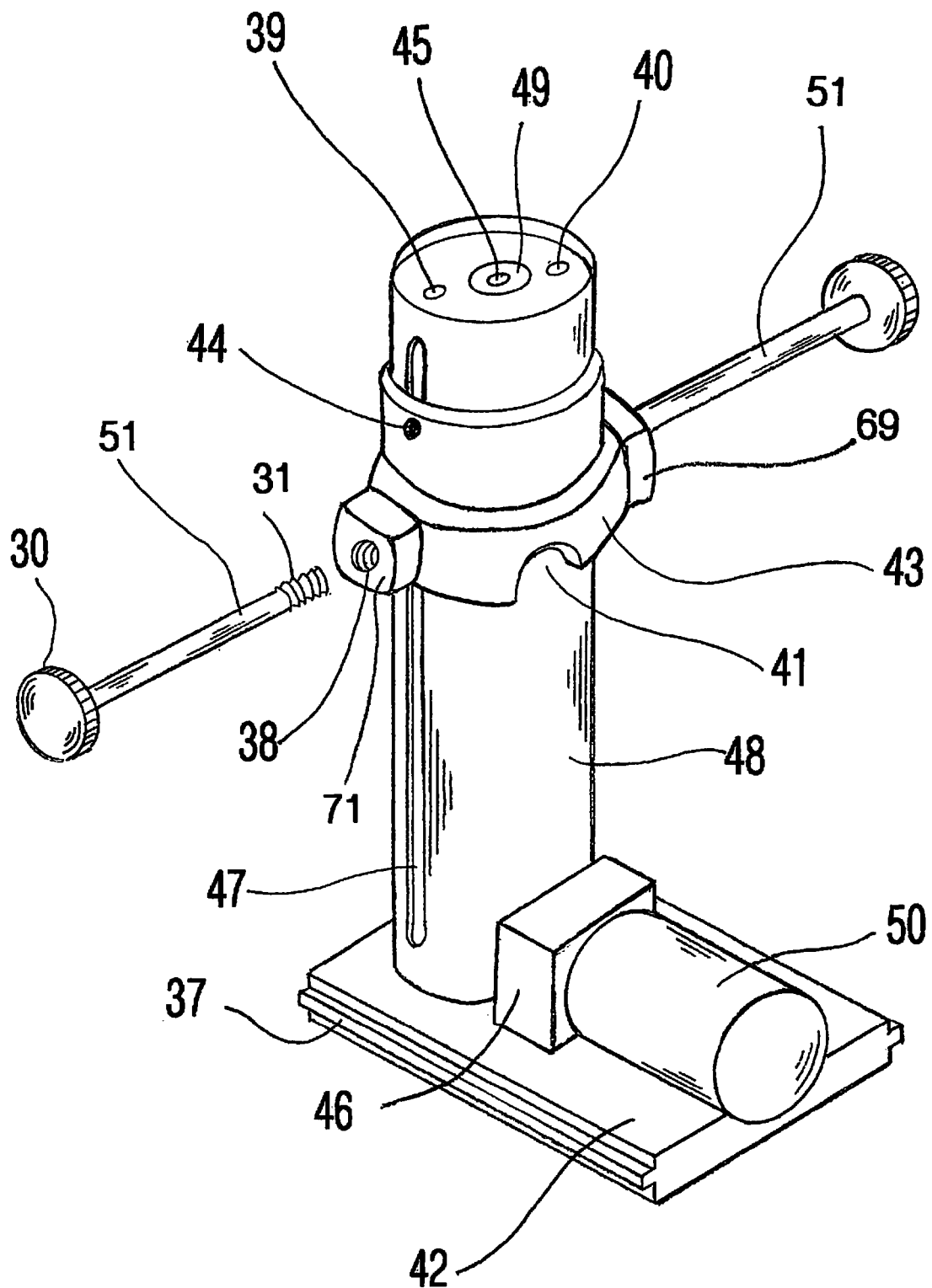
FIG. 4 is a perspective view of the central post, its motor and lifting transverse rods.

Turning now to FIG. 3, which provides details of the baseplate 8 and the moving torso plate 17. The later having corner extension 19 and 29 conveniently removable prior to surgery and corresponding to the right or left operated hip. The removable wedges are securely attached to the torso plate 17 by two stabilizing pins 33 and a locking rod 51, having a threaded medial end 34 and lateral turning knob 35. When torso plate 17 is elevated by the lifting mechanism of the central post 5, the proximal edge (toward the head of the patient) will slide over baseplate 8. Ball bearing wheels situated at the end of the baseplate are for rolling into groove 22 will facilitate the smooth sliding of the torso plate. In addition, the baseplate 8 provides right and left lateral extensions 20 having a slot 21 for using conventional buckle (not shown) for securing to the side railing of the operating table. Furthermore, the torso plate provides circular recess 26 for receiving central post 48 (FIG. 4). In addition, the baseplate provides square recess 23 having longitudinal locking grooves 25. Said recess will receive central post 5 where its base 42 and tongue 37 will interlock with groove 25 in a tongue and groove fashion.

Referring now to FIG. 4, which depicts central post 48 and gliding lifting ring 43 with lateral extensions 69 and 71. Said lateral extensions having threaded holes 38 for receiving the threaded portion 31 of lifting rods 51. Furthermore, gliding lifting ring 43 provides a recessed notch 41 to accommodate the rotating shaft of the motor when the lifting ring travels all the way down. Additionally, motor unit 50 and gear box 46 are firmly attached onto base 42 of central post 48. Said base 42 having a longitudinal tongue on the side for insertion into groove 25 of baseplate 8 (see FIG. 3). This allows the gliding lifting ring 43 to travel up and without rotation, while guiding pin 44 sliding in groove 47 provides guidance.

Figure 5:
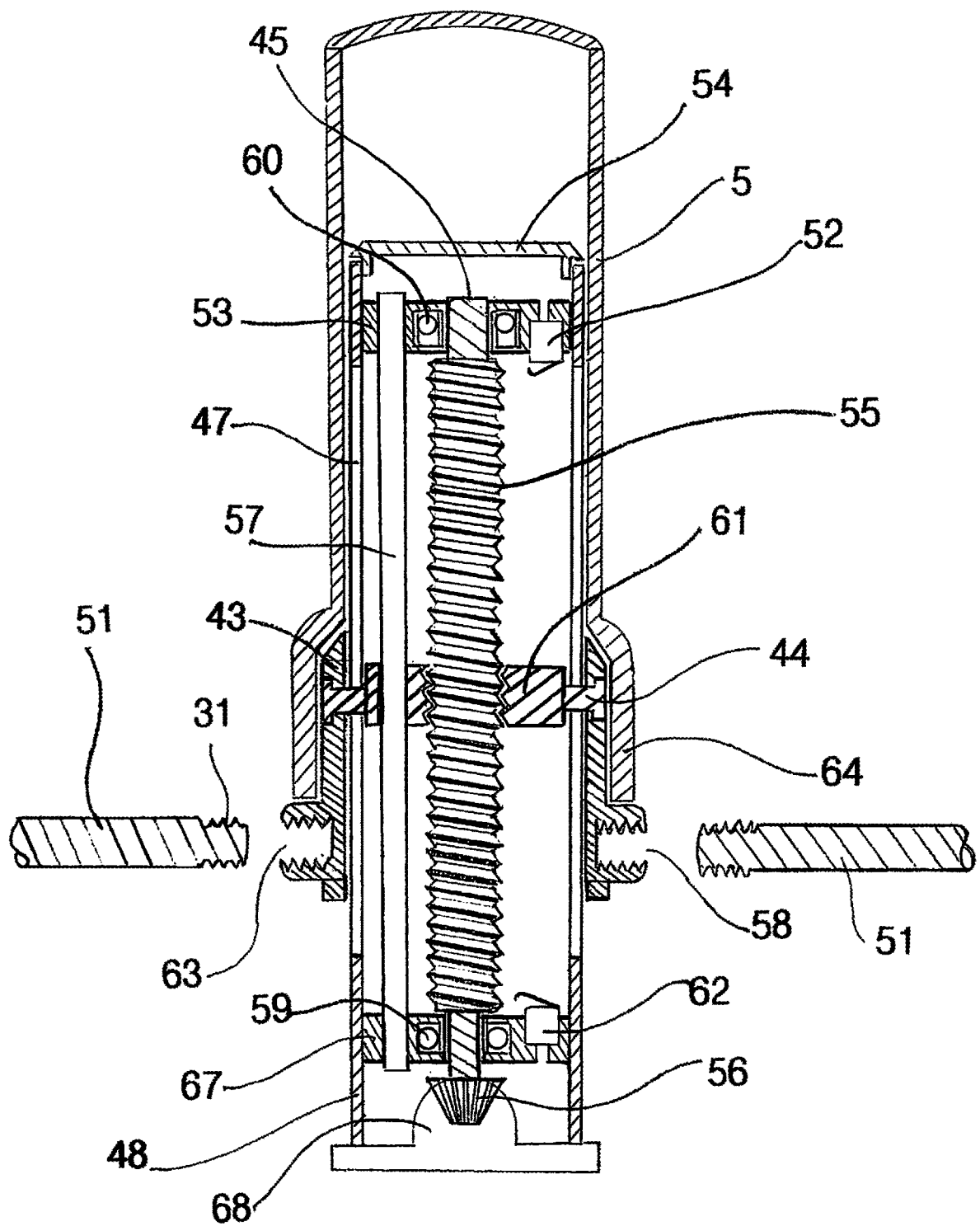
FIG. 5 is a sectional view of the central post showing the rotating threaded bar.

FIG. 5 illustrates the lifting mechanism. Rotating central threaded shaft 55 is secured within central post 48. The proximal end of central threaded shaft 55 is secured to disc 53 and the distal end of central threaded shaft 55 to disc 67. In one embodiment, ball bearings 59 and 60 allows central threaded shaft to rotate freely. In another embodiment highly polished bushings may be used. Threaded lifting carriage 61 is threaded onto the rotating shaft. Threaded lifting carriage travels up or down when threaded shaft 55 turns. To prevent over travel of the threaded lifting carriage 61, proximal 52 and distal 62 disconnects are provided. Stationary channel 57 allows passage of the electric wires and connections. A beveled gear at the lower end of the threaded shaft is connected to the gearbox of the motor through recess 68. The gliding lifting ring 43 will receive post 5, inserted over central post 48, which will travel upward when the lifting mechanism is activated.

Figure 6:
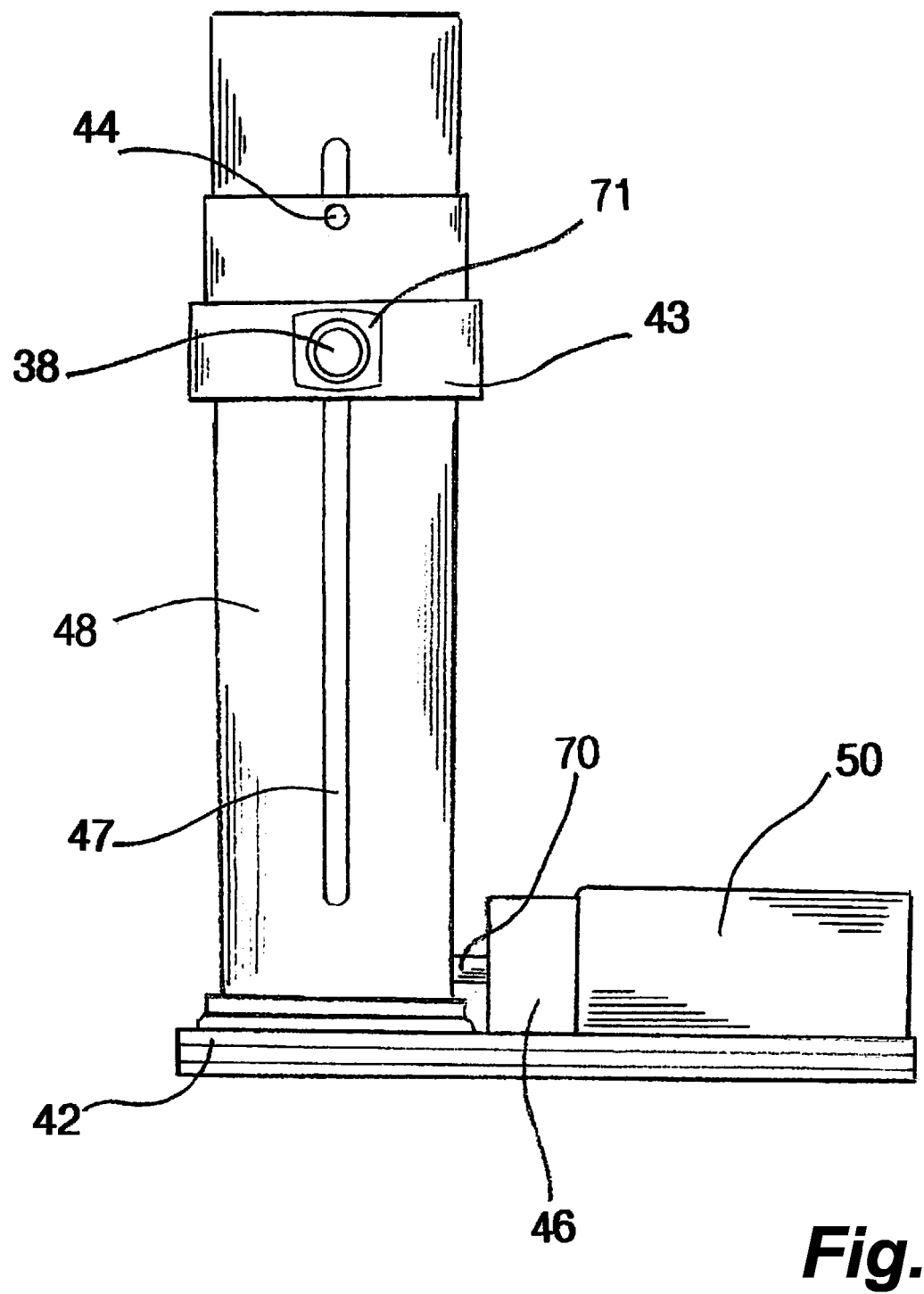
FIG. 6 is a side view of the central post, showing the sliding carriage and motor.

Turning now to FIG. 6, where lifting ring 43 is guided upward by guiding pin 44 sliding into slot 47 over the central post 48. Motor 50 drives gearbox 46 and a transmission shaft 70 to accomplish the lifting effect.

The patient is placed supine on the device of the present invention. The corner extension 29 on the operated side is removed and the lower extremity attachment is placed in position by securing it in position using rod 51, which is passed in the proximal portion of the attachment and threaded in opening 38 situated in the lateral extension 71 of lifting ring 43

Figure 7:
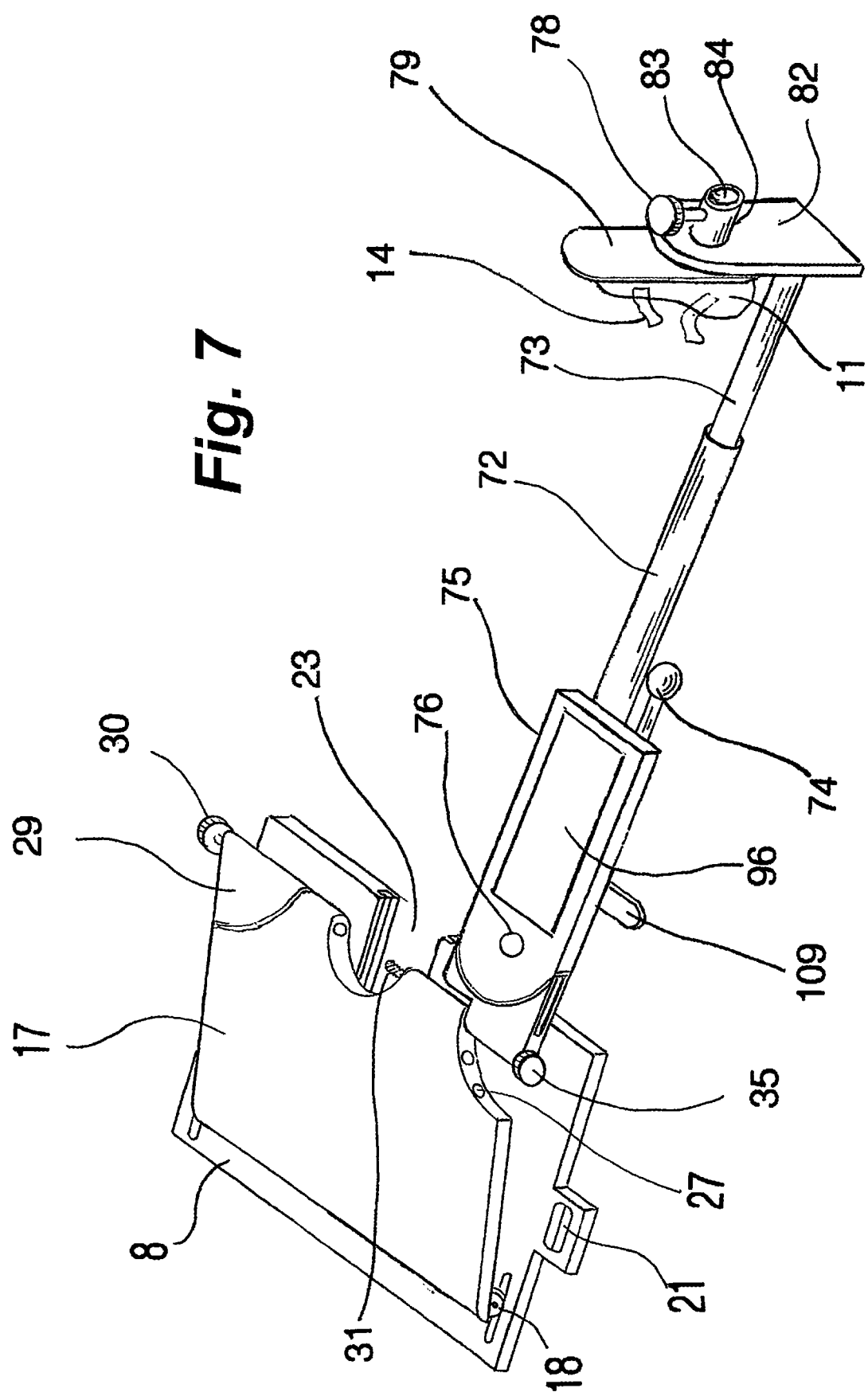
FIG. 7 is a perspective view of the lower extremity strut with foot boot attachment.

Referring now to FIG. 7, which depicts the lower extremity attachment which provides a supporting thigh plate 75 and tubular strut member 72. Tubular strut member 72 provides a distal slidable extension 73. The proximal plate is hinged proximally via pin 76 for allowing the lower extremity attachment to swing to the right or the left in order to improve the visualization and alignment of the proximal femoral bone in order to facilitate insertion of straight instrument into the medullar canal of the femur. Furthermore, the supporting plate 75 provides a central portion 77, which can be raised proximally thereby applying pressure on the posterior surface of the thigh. Said pressure is transmitted via soft tissue and musculature of the thigh to the femoral bone, which will cause the femur to be elevated and its proximal end to protrude into the skin incision. Technically, the surgeon will facilitate the process by releasing some additional soft tissue including joint capsule.

Figure 8:
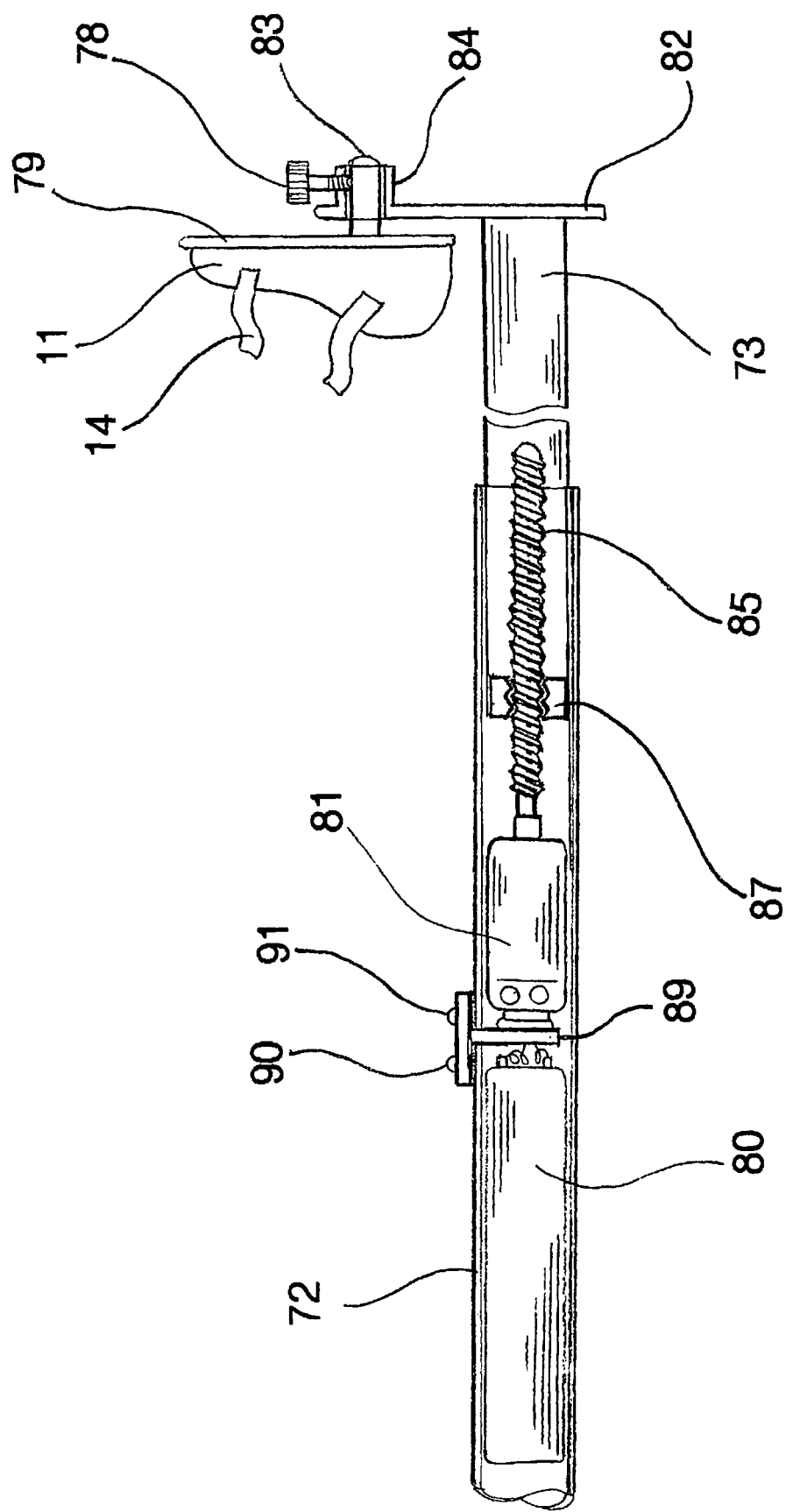
FIG. 8 is a sectional view of the strut showing the motorized traction mechanism.

FIG. 8 shows a motorized traction/distraction mechanism. Distal traction of the foot is accomplished using motor 81 located inside tubular strut member 72. Motor 81 has a threaded shaft 85. Threaded corresponding carriage 87 is firmly attached to the inner wall of said distal slidable extension 73. Threaded corresponding carriage 87 for moving said distal slidable extension 73 distally or proximally when said motor 81 activated to turn clockwise or counterclockwise.

Figure 10:
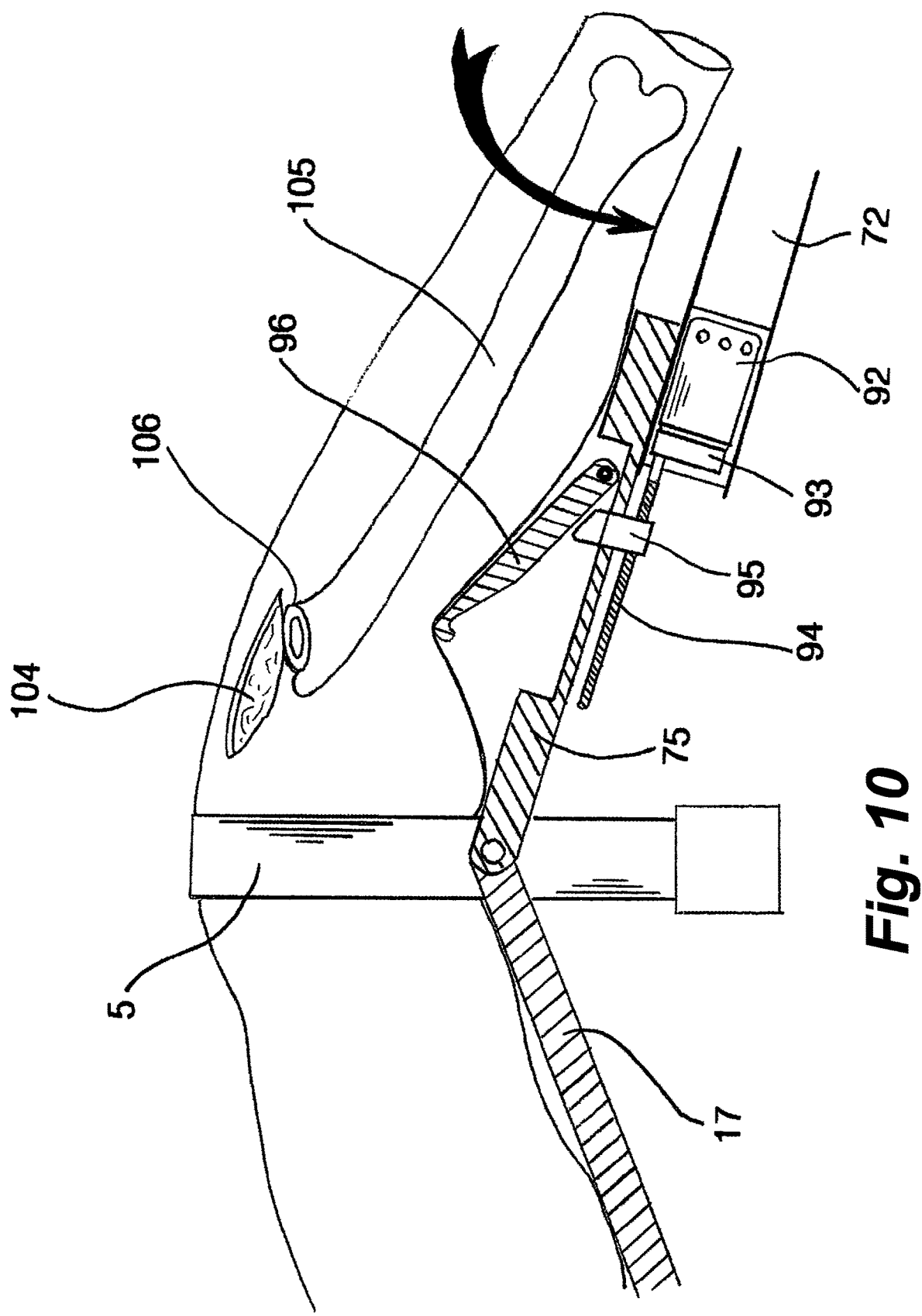
FIG. 10 is a side view of the motor-powered femoral elevator in the elevated position.

In one embodiment, a battery is approximately situated in said tubular strut member 72. Electrical connector 89 having control switches 91 for distraction and 90 for approximation is conveniently located on tubular strut 72 and easily felt by the surgeon under the sterile surgical drapes, thereby eliminating the need for surgical assistant to apply traction to the foot unit. In different embodiment, the operating surgeon can easily use a foot pedal to accomplish the control of the distraction/retraction motor 81. During the surgical procedure, it is desirable after the resection of the femoral head to externally rotate the foot (as seen in FIG. 10), this will provide better position of the femoral bone for inserting reamers into the femoral medullary canal. This can be easily accomplished by loosening knob 78 (FIG. 7) in order to release tension on stud 83 (situated within tube 84) and allowing footplate 79 of boot 11 to be turned 90° degrees externally and secured by tightening knob 78.

Figure 9:
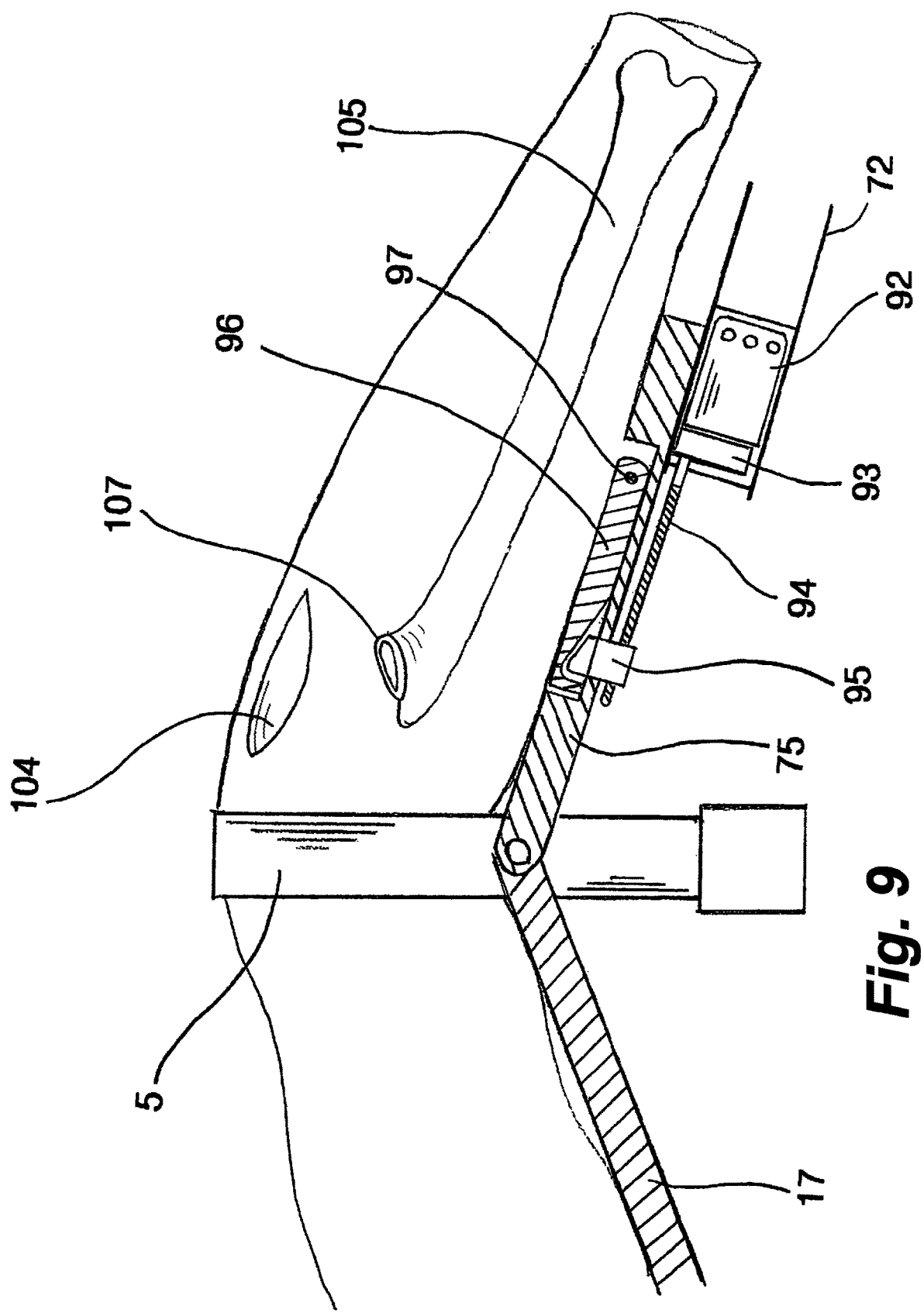
FIG. 9 is a side view of the motor-powered femoral elevator in the retracted position.

Referring now to FIG. 9, which depicts a sectional side view of the invented device showing the mechanism of the femoral bone elevator 96, comprising motor 92 with its gear box 93 and threaded cam 94 which will mechanize lifting wedge 95. As the latter is pulled distally by the motor it will slide under the femoral elevator plate 96 causing its proximal end to raise and elevate the femoral bone so its proximal end 107 will protrude through the surgical incision 104.

Referring now to FIG. 10, which depicts a side sectional view of the femoral elevator mechanism, the distal movement of the lifting wedge 95 will slide under the femoral plate 96 causing it to rise and push up the femoral bone 105 and its proximal end 106 closer to the skin incision 104. When the operation is complete, reversing the motor 92 moves the sliding wedge 95 proximally causing the femoral elevator to come down and becomes flat and level with the thigh plate 75. FIG. 10 clearly show the external rotation of the femur which will improve alignment of the cut femur vis a vis the surgical incision.

Figure 11:
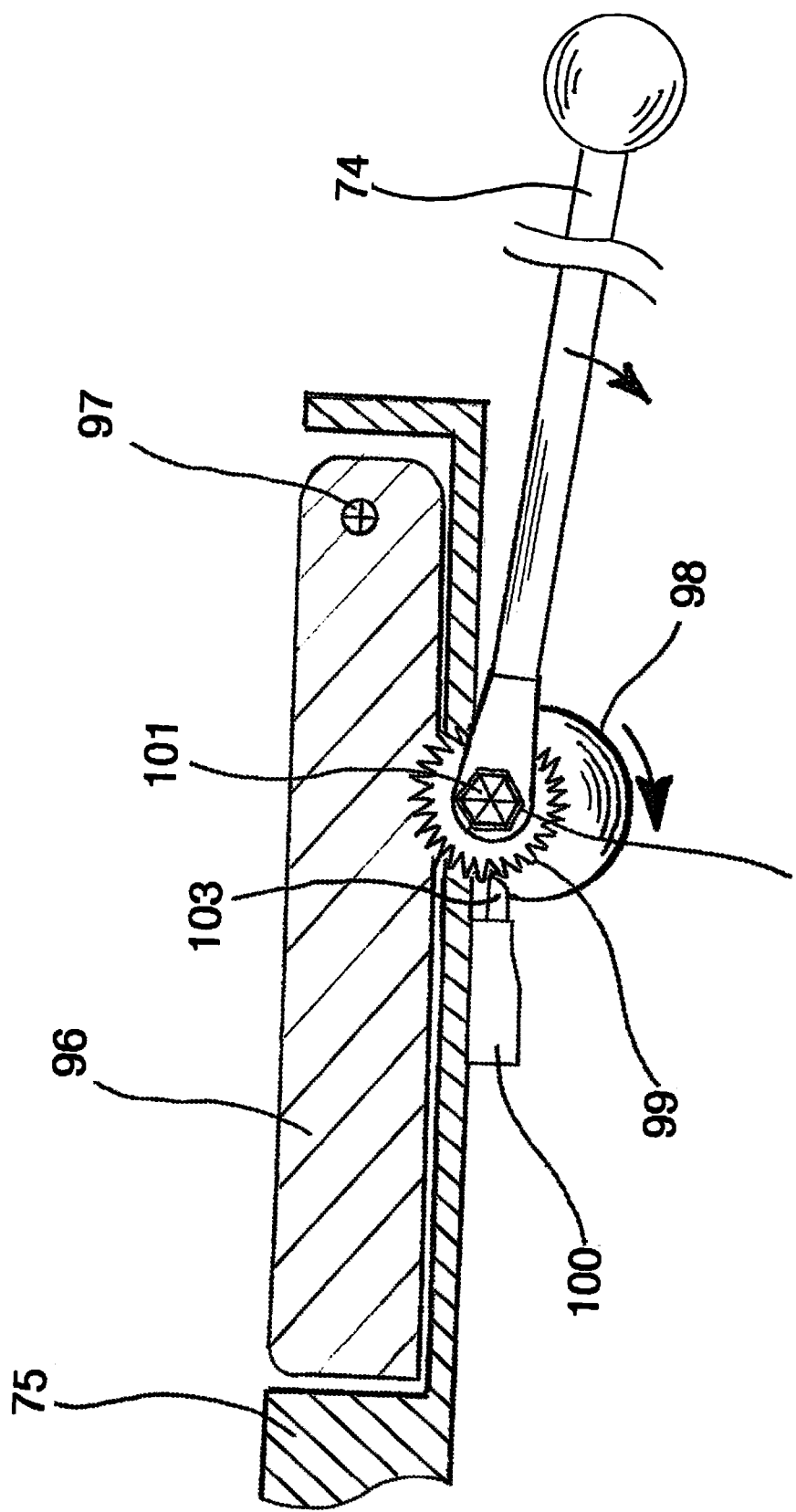
FIG. 11 is a side view of the manually operated femoral elevator in retracted position.

Turning now to FIG. 11, which depicts an embodiment where the femoral elevator mechanism is mechanical, and hand driven rather than motorized. As can be seen, the femoral elevator plate 96 is hinged with pin 97. A lifting roll 98 in contact with the lower surface of the femoral elevator plate 96, provides an eccentric axial rod 101 going through the roll 98. In one embodiment, axial rod 101 has an octagonal cross section to preventing rotation inside lifting roll 98. Axial rod 101 is easily slidable inside lifting roll 98.

Furthermore, a cogwheel 99 is firmly attached to lifting roll 98. In one embodiment, spring-loaded tongue 103 (see FIG. 11) may be actuated by a spring inside enclosure 100. Enclosure 100 is fixed to thigh plate 75. The tongue will allow rotation of the cogwheel in clockwise direction only and prevent backlash.

A ratchet wrench 102 that conformably fits over octagonal axial rod 101 may be used to rotate lifting roll 98 when its handle 74 is pushed down.

Figure 12:
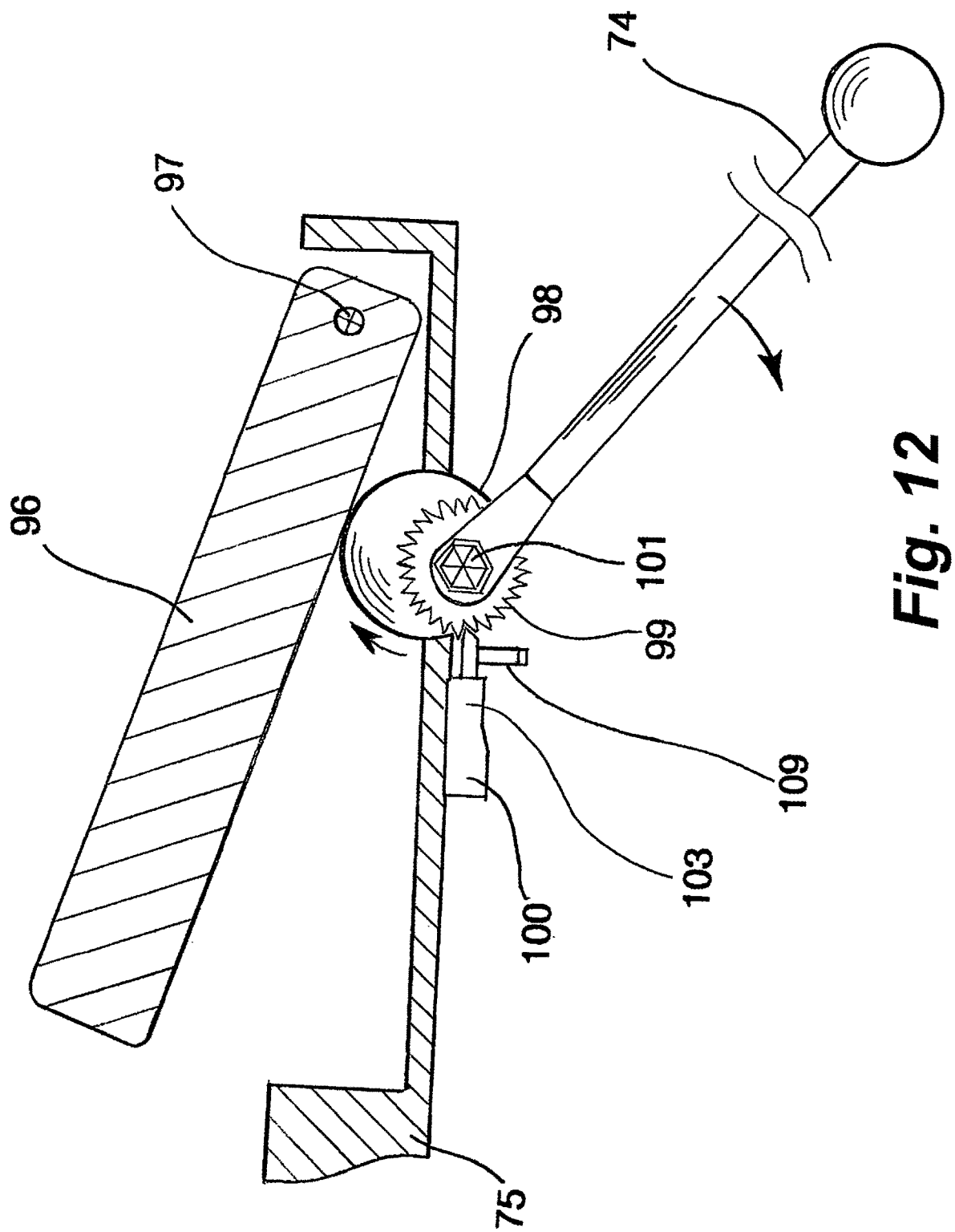
FIG. 12 is a side view of the manually operated femoral elevator in elevated position.

Referring now to FIG. 12, shows one embodiment of a manual mechanism of the femoral elevator. When ratchet wrench lever 74 is lowered, lifting roll 98 rotates clockwise. Since the roll has eccentric rotation axis, it will cause the elevator plate to rise. Ratchet wheel 99 will prevent the lifting roll from going backward. Release lever will retract the tongue allowing the lifting roll to turn counterclockwise and return to the flat position.

The disclosed embodiments provide a surgical table attachment adapted for usage with a common operating table that facilitates the surgical approach to the proximal end of the femoral bone after the removal of the femoral head. The surgical table attachment maybe constructed from any metallic alloy, plastic, or composite material. For example, it may be constructed of radiolucent material allowing intraoperative X-ray control. It maybe also be constructed from materials making the device is disposable, after a single use.

It should be understood that this description is not intended to limit the embodiments. On the contrary, the embodiments are intended to cover alternatives, modifications, and equivalents, which are included in the spirit and scope of the embodiments as defined by the appended claims.

Although the features and elements of aspects of the embodiments are described being in particular combinations, each feature or element can be used alone, without the other features and elements of the embodiments, or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

The above-described embodiments are intended to be illustrative in all respects, rather than restrictive, of the embodiments. Thus, the embodiments are capable of many variations in detailed implementation that can be derived from the description contained herein by a person skilled in the art. No element, act, or instruction used in the description of the present application should be construed as critical or essential to the embodiments unless explicitly described as such.

Alternate embodiments may be devised without departing from the spirit or the scope of the different aspects of the embodiments.

The surgical table attachment as described maybe constructed from any metallic alloy, plastic, or composite material. For example, it may be constructed of radiolucent material allowing intraoperative X-ray control. It maybe also be constructed from materials so that it the device is partially or totally disposable, after a single use.

What is claimed:

1. A surgical folding operative table attachment device comprising:
    a proximal torso supporting flat plate;
    a baseplate;
    a lower extremity supporting plate;
    a foot strut attachment;
    a central lifting mechanism;
    a femoral bone lifting device;
    an outer sliding cylinder;
    a threaded central rotating shaft; and
    a threaded lifting carriage for traveling vertically along said threaded central shaft when it rotates.

2. The table attachment device of claim 1, wherein said proximal torso supporting plate further comprises right and left conveniently removable corner extensions for supporting the right or left hip, said extensions being secured to said supporting torso plate with stabilizing rods and threaded pins.

3. The table attachment device of claim 1, wherein said proximal torso supporting plate is connected to said lower extremity supporting plate via a removable hinge.

4. The table attachment device of claim 1, wherein said proximal torso supporting plate further comprises a central recess for accepting lifting mechanism.

5. The table attachment device of claim 1, wherein said baseplate further comprises:
    two lateral slotted extensions for securing said table attachment device to an operating table; and
    two or more longitudinal grooves situated along the top surface of said baseplate for receiving guiding wheels of the torso supporting plate when lifting mechanism is activated.

6. The table attachment device of claim 1, wherein said baseplate provides slotted lateral extensions of appropriate size and location for securing the device to the side rails of the operating table.

7. The table attachment device of claim 1, further comprising:
    a hinge pivotally linking said proximal torso supporting flat plate and said lower extremity supporting plate, wherein said lower extremity supporting plate supports the patient's thigh.

8. The table attachment device of claim 1, wherein said foot strut attachment is firmly attached to the bottom of the lower extremity supporting plate and consists of tubular strut member having and distal slidable extension slidable inside said tubular strut member.

9. The table attachment device of claim 1, wherein said central lifting mechanism is slidably secured into the central portion of said baseplate using a tongue and groove configuration.

10. The table attachment device of claim 1, wherein said foot strut has a tubular strut member, said tubular strut member firmly secured under the surface of the lower extremity supporting plate and said tubular strut member having a distal slidable extension.

11. The table attachment device of claim 10, further comprising, a traction/distraction mechanism having:
    a motor located inside said tubular strut member, said motor having a threaded shaft; and
    a threaded corresponding carriage firmly attached to the inner wall of said tubular strut member for moving said tubular strut member distally or proximally when said motor activated to turn clockwise or counterclockwise.

12. The table attachment device of claim 10, wherein the distal slidable extension member including a foot restraining means for attachment comprising a flexible boot having securing straps, said foot restraining attachment configured to allow rotation to the right or the left; and
    a locking knob for subsequently locking the foot in position.

13. The table attachment device of claim 1, wherein said threaded lifting carriage is attached to a gliding lifting ring, said ring providing two threaded diametrically opposed rods used to make the hinges between the torso plate and the lower extremity supporting plate, wherein when the threaded lifting carriage is lifted it will subsequently raise the gliding lifting ring as well as two diametrically opposed threaded rods.

14. The table attachment device of claim 1, wherein said threaded lifting carriage is attached to a gliding lifting ring via two lateral pins which slide into vertical slots.

15. The table attachment device of claim 1, wherein said femoral bone lifting device comprises:
    a lower thigh supporting plate to provide a central longitudinal section which is hinged distally (toward the foot) and can be raised proximally providing pressure on the posterior surface of the thigh and pushing the femoral bone up where its proximal end will be brought up closer to the surgical wound.

16. The table attachment device of claim 15, further comprising:
    an elevator plate;
    a tubular strut; and
    a wedge having an upper sloping surface for contacting the lower surface of said femoral elevator plate, wherein sliding said wedge distally lifts said elevator plate and reversing the travel of said lifting wedge lowers said femoral elevator plate.

17. The table attachment device of claim 16, further comprising:
    a motor located inside said tubular strut to mechanically slide said wedge underneath and thereby raise or lower said femoral elevator plate; and
    a foot pedal for allowing the operating surgeon to electronically control said motor.

18. The table attachment device of claim 15, further comprising:
    an elevator plate; and
    a lifting roll having an eccentric transverse axis of rotation, varying the distance between the eccentric center and the point of contact with the undersurface of said elevator lifting causes the said plate to rise or to come down.

19. The table attachment device of claim 18, wherein said lifting roll has an octagonal axial rod configured to accept a removable ratchet wrench for manual actuation by the operating surgeon, and wherein said lifting roll includes a solidary ratchet and a spring-loaded release tab which acts as a stop to prevent backlash.

\* \* \* \* \*